United States Patent [19]
Hutchins et al.

[11] Patent Number: 6,068,393
[45] Date of Patent: May 30, 2000

[54] ROBOTIC SYSTEM FOR PROCESSING CHEMICAL PRODUCTS

[75] Inventors: Burleigh M. Hutchins, Upton; Tye B. Fowler, Bellingham; David R. Friswell, Upton; Paul A. Kearsley, Hopedale; Bruce A. Swanson, Mansfield; Eugene T. Tetreault, Sutton, all of Mass.; Jack Elands, Oberhaslach, France

[73] Assignee: Zymark Corporation, Hopkinton, Mass.

[21] Appl. No.: 08/964,951

[22] Filed: Nov. 5, 1997

[51] Int. Cl.[7] ..................................................... G06F 19/00
[52] U.S. Cl. ............................... 364/468.19; 364/478.16; 422/67
[58] Field of Search ........................... 364/468.19, 468.2, 364/468.21, 478.01, 478.16; 436/47, 48; 422/62, 63, 67

[56] References Cited

U.S. PATENT DOCUMENTS

| | | | |
|---|---|---|---|
| 5,056,028 | 10/1991 | Ohta et al. | 364/468.2 |
| 5,150,288 | 9/1992 | Imai et al. | 364/132 |
| 5,255,197 | 10/1993 | Iida | 364/132 |
| 5,463,564 | 10/1995 | Agrafiotis et al. | 364/496 |
| 5,578,269 | 11/1996 | Yaremko et al. | 422/64 |

*Primary Examiner*—Paul P. Gordon
*Attorney, Agent, or Firm*—John E. Toupal; Harold G. Jarcho

[57] ABSTRACT

A robotic system for processing a plurality of products, the system including a plurality of units arranged to sequentially receive the products and each having a work station for effecting a specific operation on the products; and a robotic device associated with each unit and operable to sequentially obtain the products from a preceding unit, to transport the products to the work station of its associated unit and to transport the products from the associated work station to a position accessible to a robotic device of a succeeding unit.

23 Claims, 9 Drawing Sheets

ROBOTIC SYSTEM FOR PROCESSING CHEMICAL PRODUCTS

BACKGROUND OF THE INVENTION

This invention relates generally to product processing systems and, more particularly, to a system for processing products in chemical laboratories and the like.

Automated laboratory systems are used widely to reduce the costs of performing multi-step chemical production and testing procedures. Many such systems employ a robotic device to move material, parts, tools or specialized devices through variable programmed motions for the performance of a variety of tasks. In a typical operation, a robot is one module of an operating system and would interact with several other modules, which may be called work stations, to achieve the processing of chemical samples. For example, pipette stations, liquid dispensing stations, diluting stations, washing stations and incubation stations are typical stations. Examples of robotic processing systems are disclosed in U.S. Pat. Nos. 4,510,684; 4,578,764; 4,586,151; 4,835,711; 5,355,439 and 5,363,885.

The user of a robotic processing system first arranges processing stations in any convenient pattern and then instructs a robot in given processing actions. Even though programming tasks, once understood by an operator, are not intellectually challenging, the task of setting up a system to operate efficiently is laborious. As the number of stations in a system increased, the number of variables to keep in mind to avoid collisions and otherwise avoid conflicts in instruction made the task laborious even for those skilled in computer programming. In addition, many traditional robotic systems such as those used for drug screening operations utilize a single robotic device with a number of work stations which perform operations requiring various time periods and may be repeated several times in a complete process. Consequently, the movement of product samples requires complex looping and scheduling for efficient operation which typically is attained by maximizing utilization time of the robotic device. Product throughput of such systems is limited therefore, by available robotic device time.

The object of this invention is to provide a robotic system which significantly increases product throughput of chemical processes such as drug screening.

SUMMARY OF THE INVENTION

The invention is a robotic system for processing a plurality of products, the system including a plurality of units arranged to sequentially receive the products and each having a work station for effecting a specific operation on the products; and a robotic device associated with each unit and operable to sequentially obtain the products from a preceding unit, to transport the products to the work station of its associated unit and to transport the products from the associated work station to a position accessible to a robotic device of a succeeding unit. System throughput can be significantly increased by the provision of individual robotic transport devices.

According to certain features of the invention, the units are separable, modular and interchangeable units. These features enhance use flexibility of the system.

According to another feature of the invention, the position is disposed in a uniform geometrically located portion of each unit. Unit interchangeability is enhanced by the uniformly located receiving positions.

In one embodiment of the invention, the receiving position is disposed on the associated unit while in another embodiment, the position is disposed on the succeeding unit. In either embodiment, interchangeability of individual units is enhanced by the provision of uniformly located positions.

According to another feature of the invention, at least some of the units are interconnected in a rectilinear array that accommodates movement of the products in a rectilinear path. Orderly product movement is facilitated by the use of a rectilinear product travel path.

According to a further feature of the invention, each unit includes an electrical connector automatically coupled to the connectors of adjacent units in response to interconnection thereof. Assembly of a system is simplified by this feature.

According to yet another feature of the invention, the connectors of each unit include a pair of connectors shaped and arranged for connection with the connectors of straddling units and the connectors are disposed in uniform locations of each unit. Unit interchangeability is further enhanced by uniform placement of connectors.

According to still another feature of the invention, the system is a chemical screening system and the products are chemical assays. The system is particularly efficient when used in chemical screening applications.

According to an additional feature of the invention, each unit is supported on rollers to provide mobility. The rollers simplify assembly of a predetermined system arrangement.

According to another feature of the invention, the units include a corner unit connected to one end of the rectilinear array and shaped and arranged to provide movement of the products in a direction transverse to the rectilinear path. The corner unit facilitates assembly of a system in a region having space limitations.

The invention also encompasses a method for processing products and including the steps of providing a processing system with a plurality of units each having a work station for effecting a specific operation; equipping each unit with an associated robotic device; and interconnecting the units in a predetermined serial arrangement including an initial unit, a plurality of intermediate units and a discharge unit. Additional steps of the method include causing the robotic device associated with the initial unit to transport a product from its associated work station to a position accessible to a said robotic device associated with a subsequent intermediate unit; causing the robotic device associated with each intermediate unit to receive the products from a preceding intermediate unit, to transport the products to the work station associated with its discharge unit and to transport the products from its associated work station to a position accessible to the robotic device of a subsequent unit; causing the robotic device associated with the discharge unit to receive the products from a preceding unit, to transport the products to the work station associated with its unit and to transport the products to a discharge area; and effecting in each work station the operation associated therewith. The method permits a significant increase in product throughput of the system.

According to one feature of the method, the interconnecting step includes interconnecting at least some of the units in a rectilinear array. The rectilinear array facilitates an orderly transition of products.

According to another feature of the method, the interconnecting step includes the steps of interconnecting some of the units into a first rectilinear array and interconnecting other units in a second array disposed transverse to said first array. The first and second transversely oriented arrays facilitate orderly product movement in confined available space.

According to still other features of the method, the units are interchangeable and each unit is supported on rollers to provide mobility. System flexibility is enhanced by these features.

According to yet another feature, the method includes the step of changing in at least one unit the orientation of the products received in the accessible position. Reorientation of the product facilitates its proper placement in the work station.

According to additional features of the method, the system is a chemical screening system, the products are chemical assays; the method includes the steps of loading the chemical assays into individual receptacles prior to the causing steps; and the operations include incubation, receptacle washing and reagent addition operations.

DESCRIPTION OF THE DRAWINGS

These and other objects and features of the invention will become more apparent upon a perusal of the following description taken in conjunction with the drawings wherein.

DESCRIPTION OF THE PREFERRED EMBODIMENTS

Figure 1:
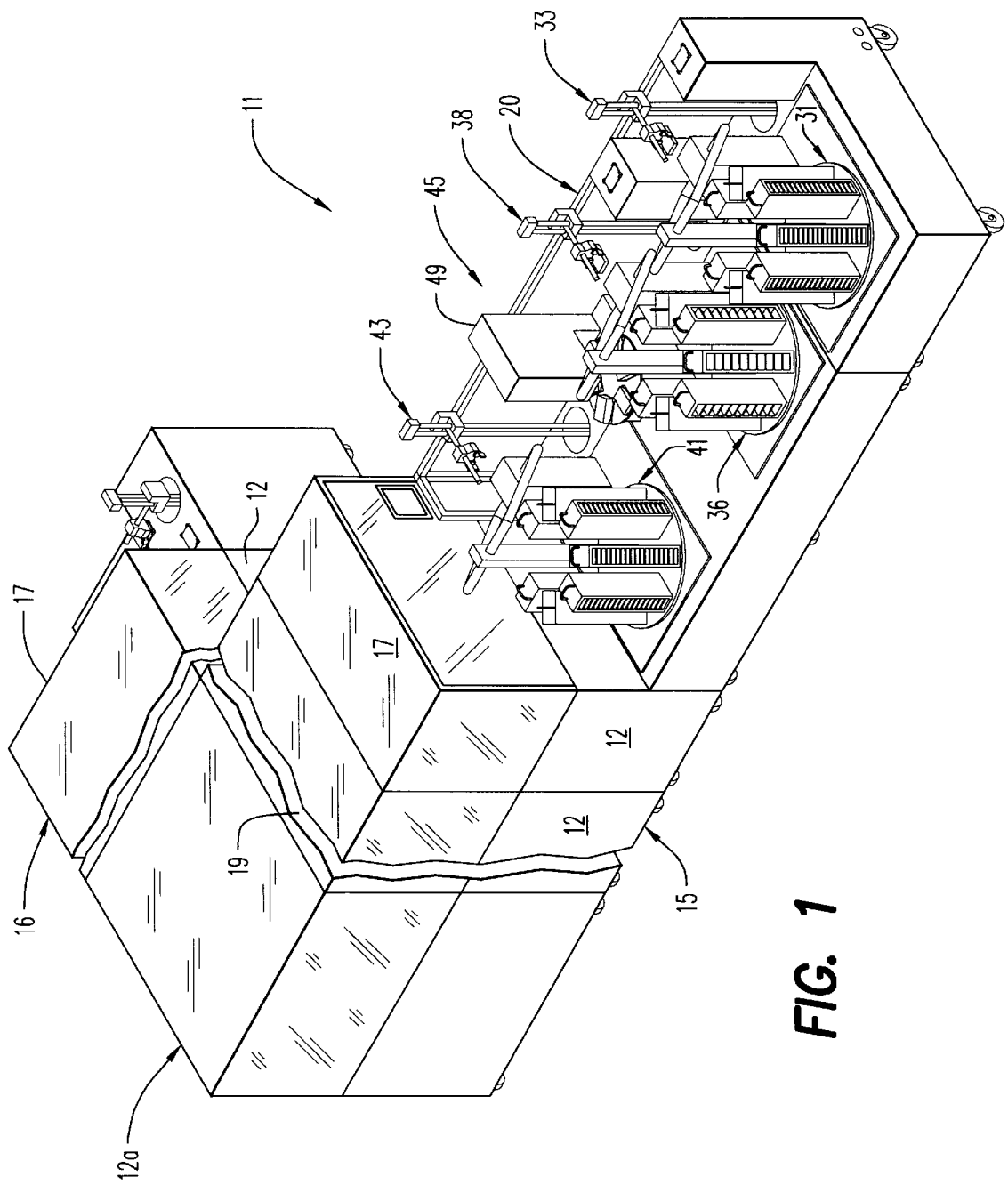
FIG. 1 is a perspective view of a robotic processing system according to the invention.
Figure 2:
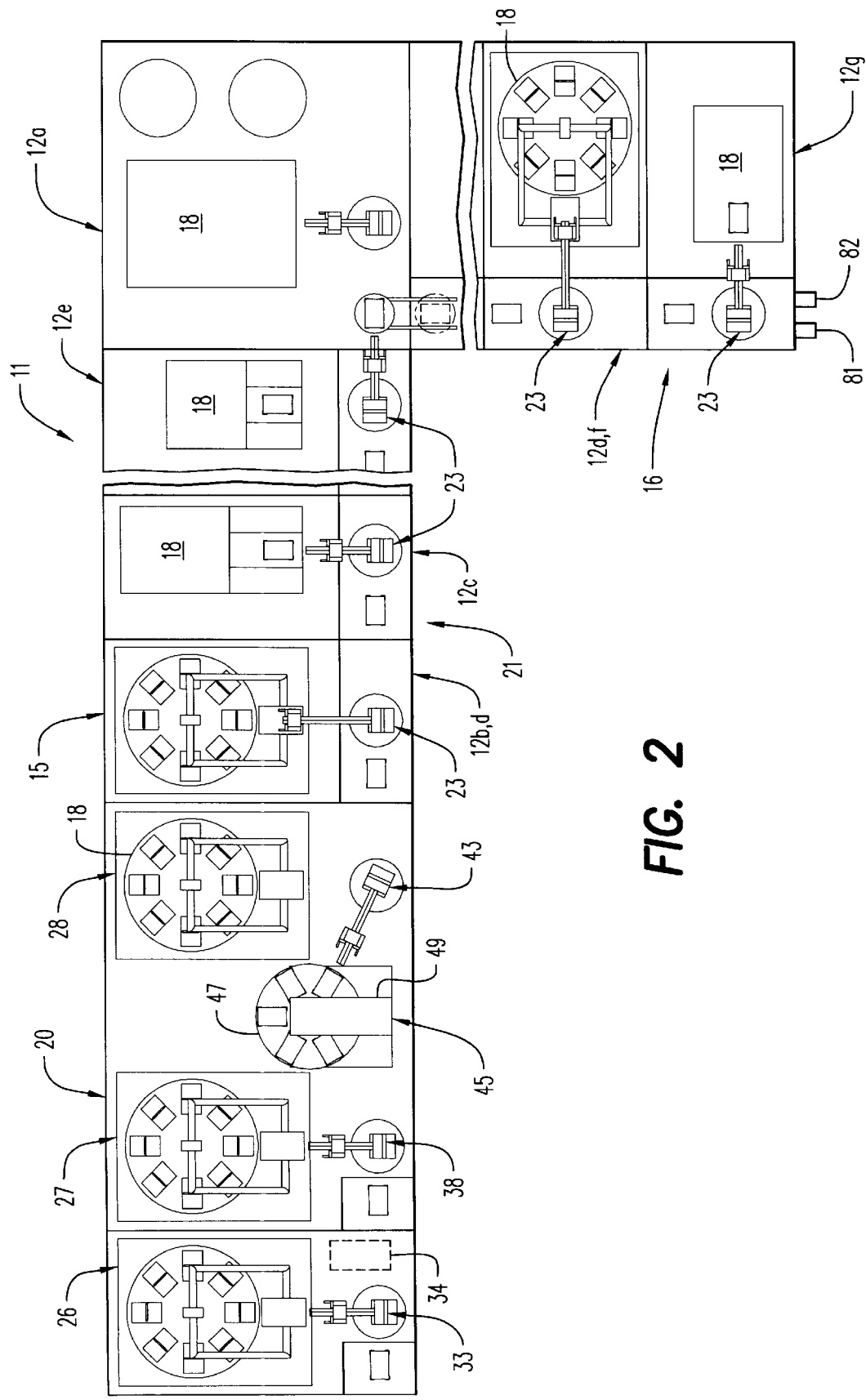
FIG. 2 is a schematic top view of the system shown in FIG. 1.

A robotic system 11 for executing a chemical screening process is illustrated in FIGS. 1 and 2. The system 11 can be used, for example, to perform immunoassays, cell-based reporter gene assays, homogeneous assays with multiple incubations, and the like. Forming the robotic system 11 are a plurality of separable, portable and interchangeable units 12 arranged to sequentially receive assay products of the screening process. One interconnected group of the units 12 are arranged in a rectilinear array 15 that accommodates assay product movement in a first rectilinear path. Another group of the units 12 is arranged in a second rectilinear array 16 which accommodates assay product movement in a direction transverse to that provided by the first array 15. Joining the first and second arrays 15, 16 is a corner unit 12a. Each of the units 12 includes a canopy 17 which engages the canopies of adjacent units. Together the canopies 17 form an enclosed environmentally controlled chamber 19 in which the chemical screening process is performed. A source unit 20 of the system 11 is connected to the initial unit 12 of the array 15.

As shown in FIG. 2, the units 12 include, in addition to the corner unit 12a, an assay product entry an incubator unit 12b, washing units 12c, incubator units 12d, reagent dispensing units 12e a discharge unit 12f and a reader unit 12g. Each of the units 12b–12g includes a conventional work station 18 for effecting a specific operation on the assay products being processed. For example, the work stations 18 of the washing units 12c execute a washing operation, the incubator units 12d have carousel racks which accommodate incubation operations, the dispensing units 12e have work stations 18 that effect a reagent dispensing operation and the reader unit 12g has a work station 18 that chemically analyzes the assay product at the conclusion of the screening process. It will be understood that the described work stations 18 are merely exemplary and that units having work stations for providing other process operations can be incorporated into the system 11.

The processing system 11 includes a transport system 21 for moving the assay products in a sequential manner through the units 12. Included in the transport system 21 is a robotic device 23 individually associated with each of the units 12b–12g. The robotic devices 23 associated with each unit 12 functions merely to transport assay products from a preceding unit to a succeeding unit. As described hereinafter, the transport system 21 is programmed to provide for each assay product a common occupancy time in the processing system 11.

Figure 3:
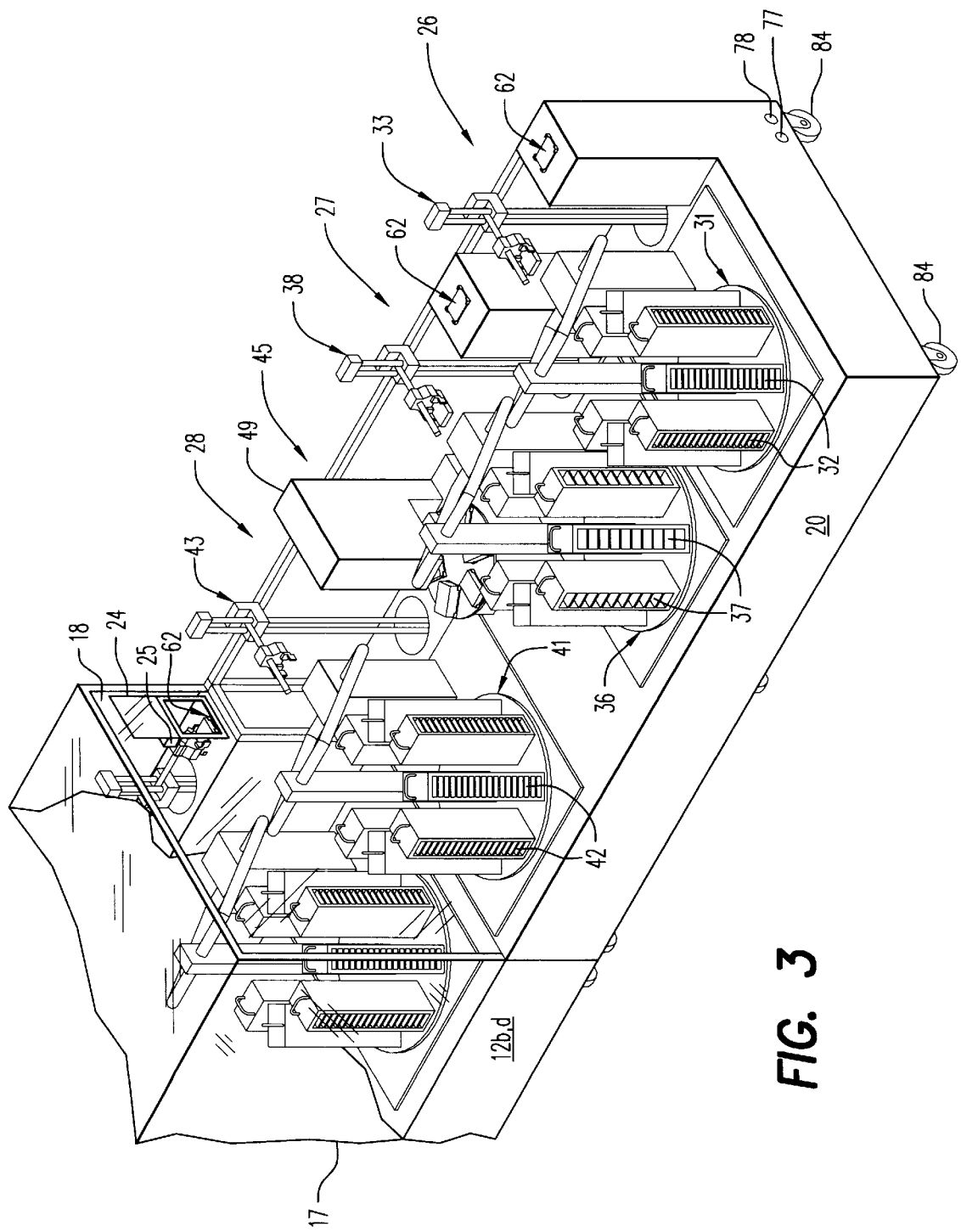
FIG. 3 is a perspective view of a source unit of the system shown in FIGS. 1 and 2.

The source unit 20 (FIG. 3) is coupled to the entry unit 12b of the system 11 but is isolated from the elongated environmental chamber 19 by a side wall 18 sealed to the canopy 17 of the entry unit 12b. Access to the unit 12b is provided by an entry door 24 which can be opened and closed by a conventional automatic actuator 25. Included in the source unit 20 are an assay supply section 26, a pipette supply section 27 and a test compound supply section 28. As shown in FIG. 3, the assay supply station 26 includes a carousel rack 31 retaining a stack of assay plates 32 and a robotic device 33 for handling thereof. A timer 34 controls operation of the robotic device 33. Similarly, the pipette supply section 27 includes a carousel rack 36 retaining stacks of holders 37 and a robotic device 38 for handling thereof. The test compound supply section 28 includes a carousel rack 41 containing stacks of compound plates 42 and a robotic device 43 for handling thereof. Straddled by the pipette source section 27 and the test compound source section 28 is a transfer station 45 shown in greater detail in FIG. 4. Structural details of the carousel racks 31, 36 and 41 are known and such units are available commercially, for example, from Zymark Corporation of Hopkinton, Mass.

Figure 4:
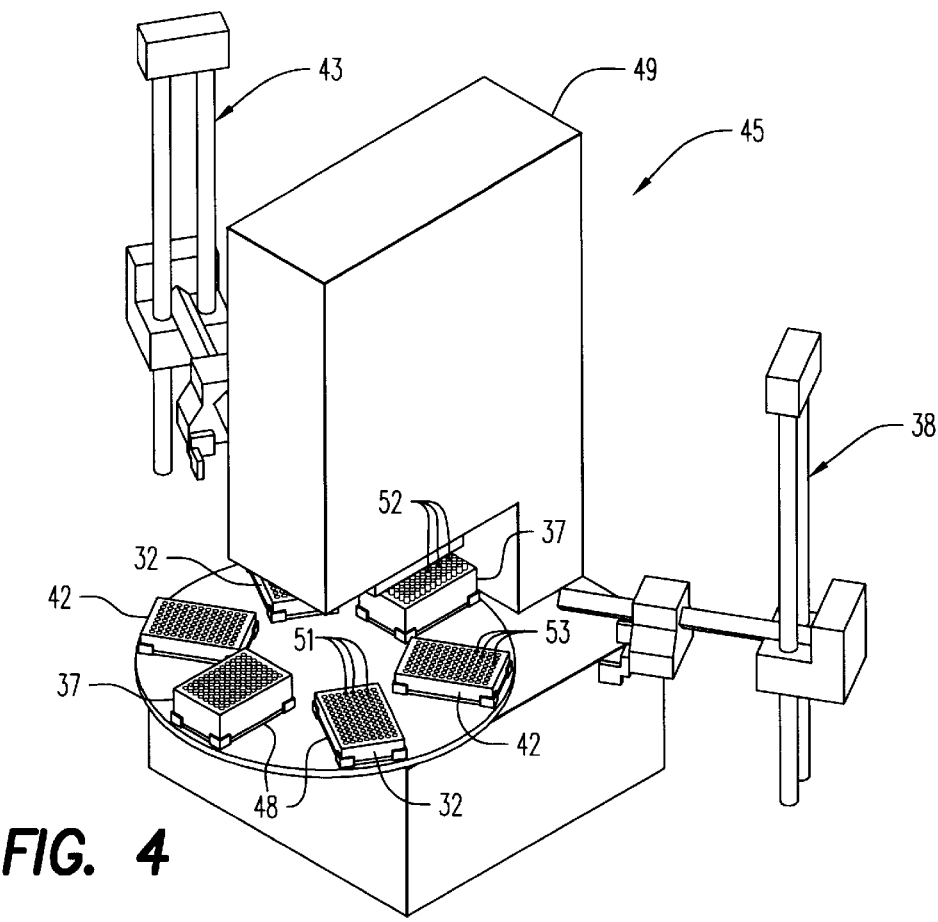
FIG. 4 is a perspective view of a transfer mechanism of the source unit shown in FIG. 3.

The transfer station 45 includes a turn-table 47 defining a plurality of annularly distributed pockets 48. Functionally associated with the turn-table 47 is a liquid withdrawal and dispensing mechanism 49. During operation of the system 11, the assay plates 32, the pipette tip holders 37 and the compound plates 42 are selectively and sequentially moved into and out of the pockets 48 by the robotic devices 38 and 43 in a manner described hereinafter. As shown in FIG. 4 each of the assay plates 32 defines an array of receptacle wells 51, each retaining an assay substance, each of the holders 37 retains an identical array of pipette tips 52 and each of the compound plates 42 retains an identical array of receptacle wells 53 each retaining a test compound.

Figure 5A:
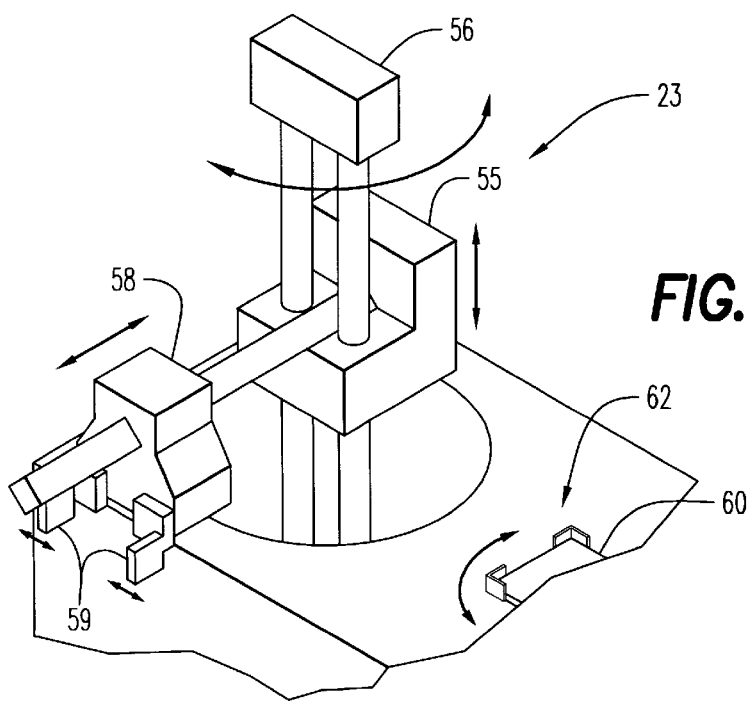
FIGS. 5a, 5b, 5c, and 5d are perspective views illustrating operation of a robotic device in one of the units of the system shown in FIGS. 1 and 2.
Figure 5B:
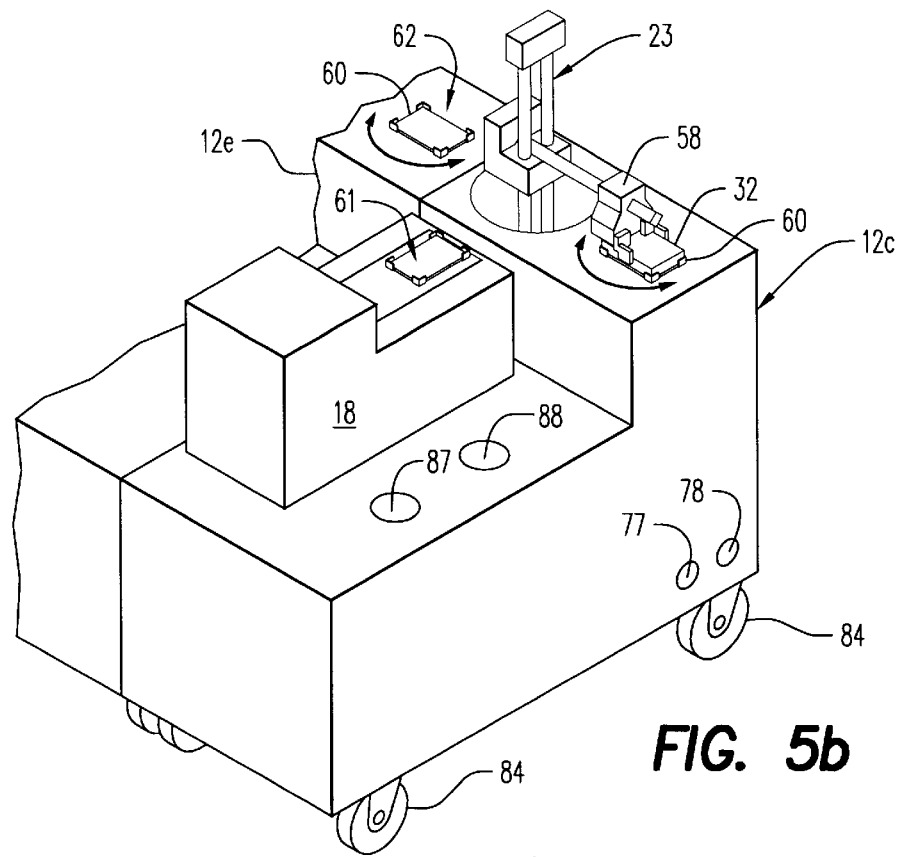
Figure 5C:
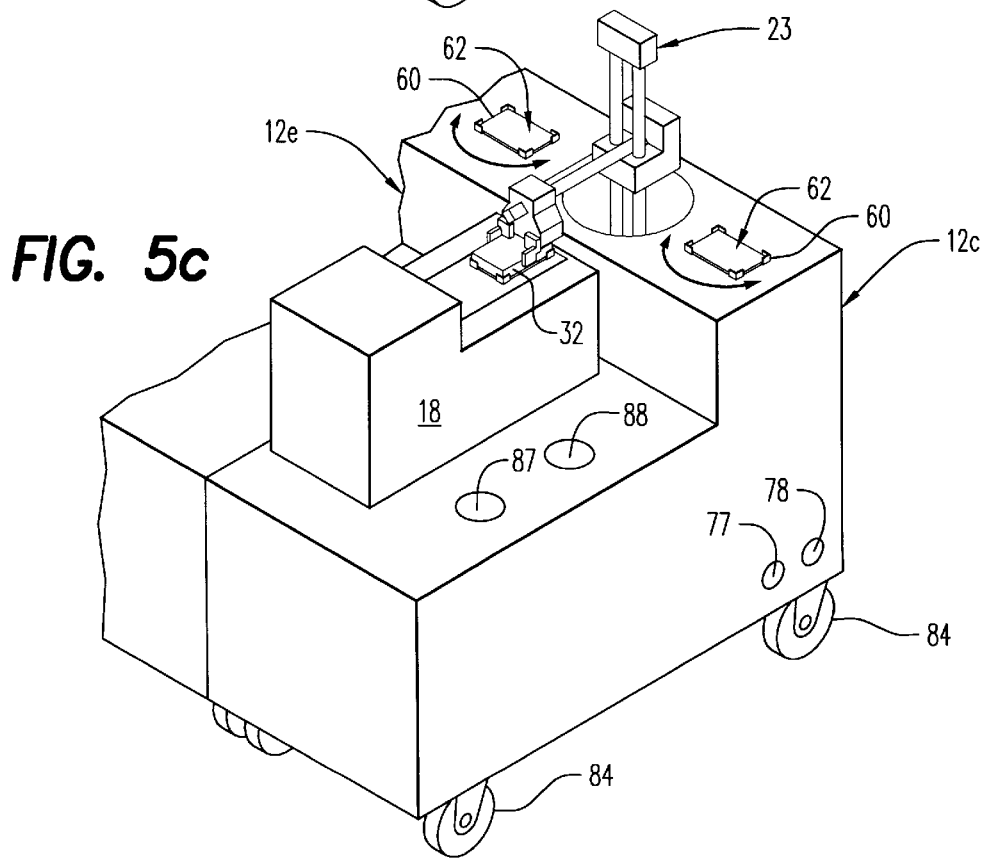
Figure 5D:
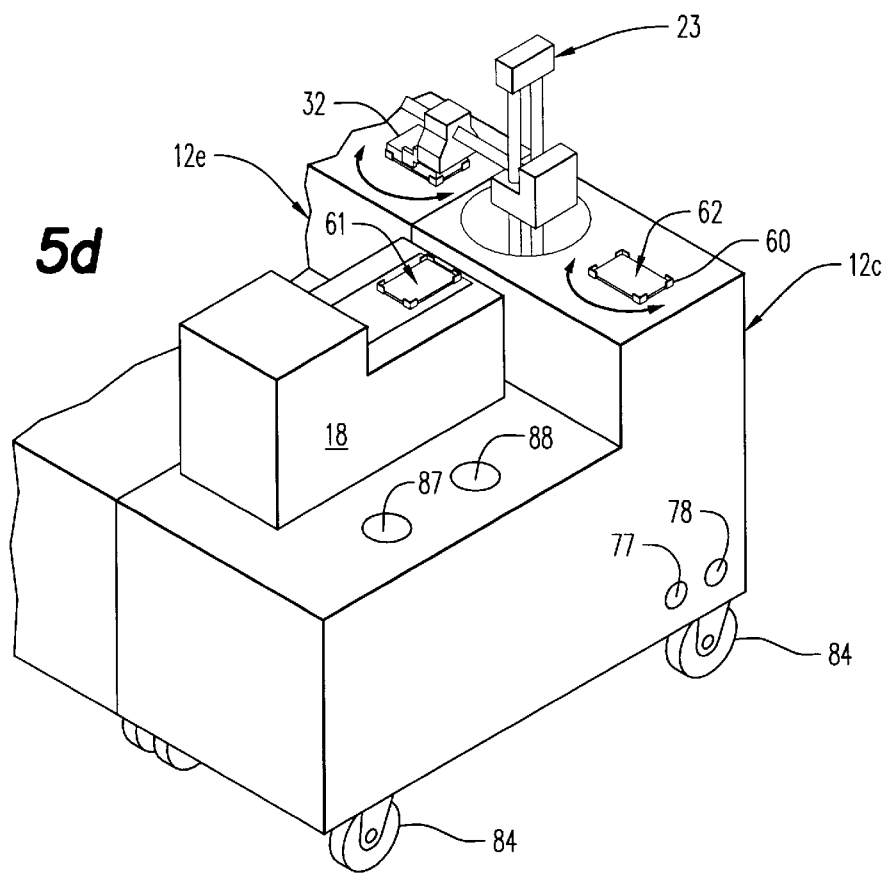

FIGS. 5a–5d depict sequential operations of the robotic devices 23. As shown in FIG. 5a, each robotic device 23 has a pedestal 55 vertically reciprocable on a vertically oriented, rotatable base member 56. Supported by the pedestal 55 is a horizontally reciprocable handling member 58 having a pair of reciprocable jaws 59. During operation of the robot 23 at each unit, the handling member 58 (FIG. 5b) first obtains from a receiving position 62 established by a rotatable turn-table tray 60 of its associated unit 12c, an assay plate 32 previously received from a preceding unit. The robot 23 then transports the assay plate 32 to an input-output position 61 of the associated work station 18, as shown in FIG. 5c. After a specific process operation is completed at the work station 18, the robot 23 transports the assay plate 32 from the input-output position 61 to a receiving position 62 on the succeeding unit 12e as shown in FIG. 5d. The tray 60 at each unit 12 can be programmed to rotate into a position which provides for a received assay plate 32 a desired changed orientation. For example, the tray 60 at each unit 12 can rotate a received assay plate 180° so as to maintain therefor the same orientation in each unit 12 of the system 11. Alternatively, re-orientation could be provided by a suitably designed robotic device 23. To accommodate selective interchange of the units 12 and simplify programming of the robotic devices 23, the receiving position 62 of each unit 12 is disposed in a uniform geometrically located portion thereof.

Figure 6:
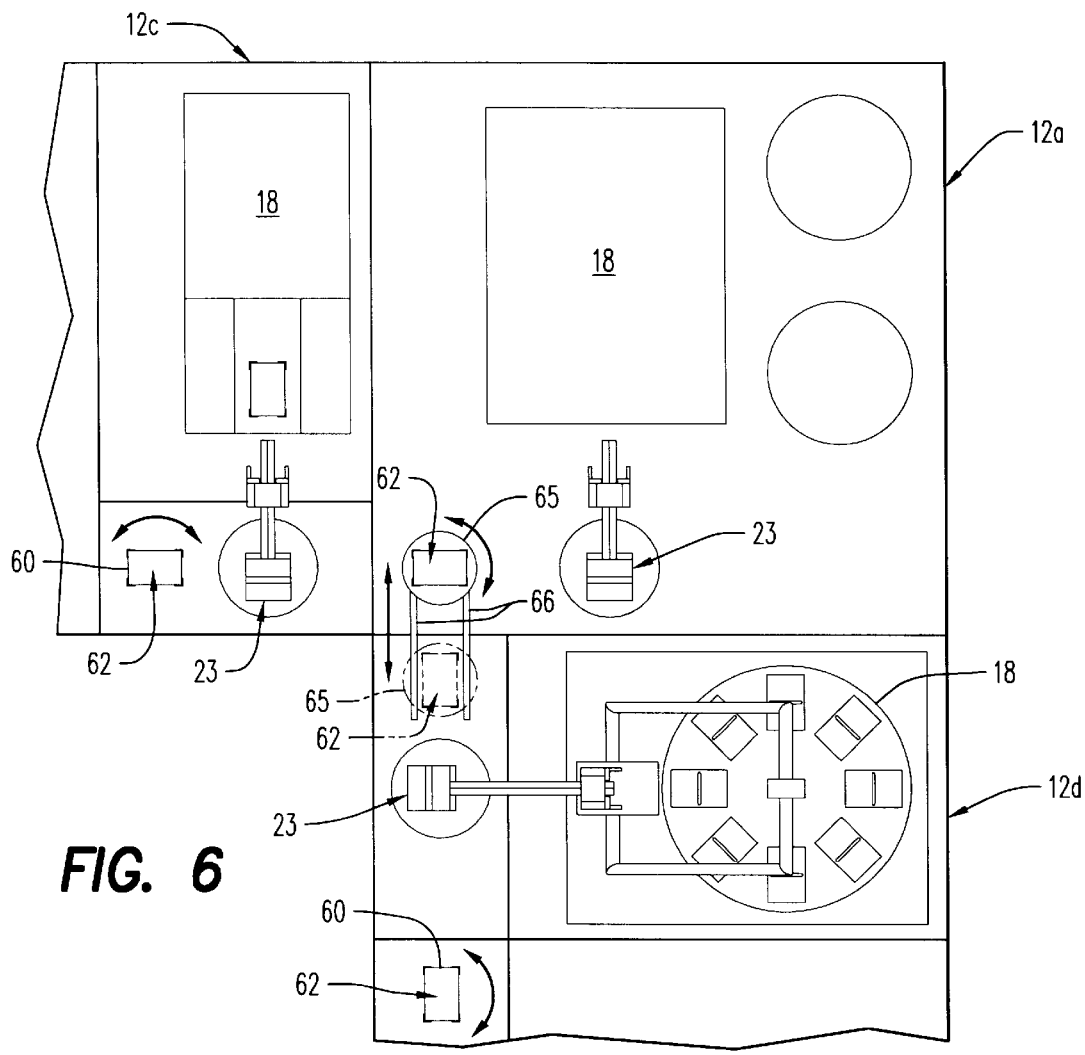
FIG. 6 is a schematic top view of a corner unit used in the system shown in FIGS. 1 and 2.

The corner unit 12a of the system 11 also has a work station 18 and cooperating robotic device 23 as shown in FIG. 6. In addition, the corner unit 12a includes a tray 65 reciprocably and rotationally mounted on a base 66. In one position shown by solid lines, the tray 65 provides for the unit 12a a uniform receiving position 62 accessible by its robotic device 23. The robotic device 23 functions as described above to transport an assay plate from the position 62 on the tray 65 to the work station 18 and after completion of an operation therein returns the plate to the position 62. After return of the assay plate, the tray 65 is moved to the uniformly disposed receiving position 62 of the succeeding unit 12d as shown by dashed lines in FIG. 6. Alternatively, the corner unit 12 can function merely to direct each assay plate 32 from the rectilinear array 15 (FIG. 2) to the transverse array 16.

Figure 7:
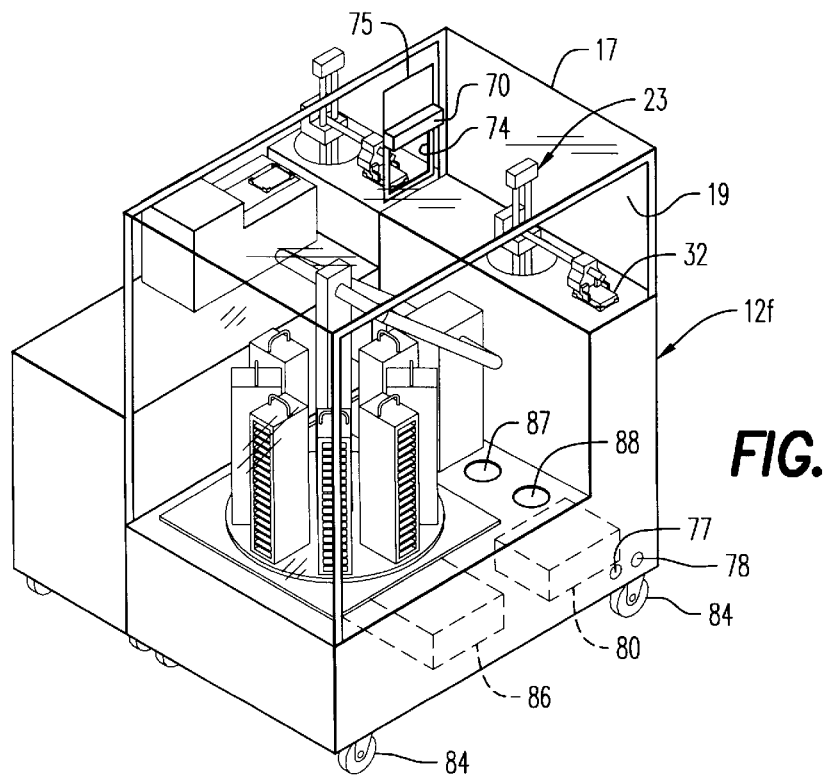
FIGS. 7a and 7 are perspective views of a discharge unit of the system shown in FIGS. 1 and 2.
Figure 7A:
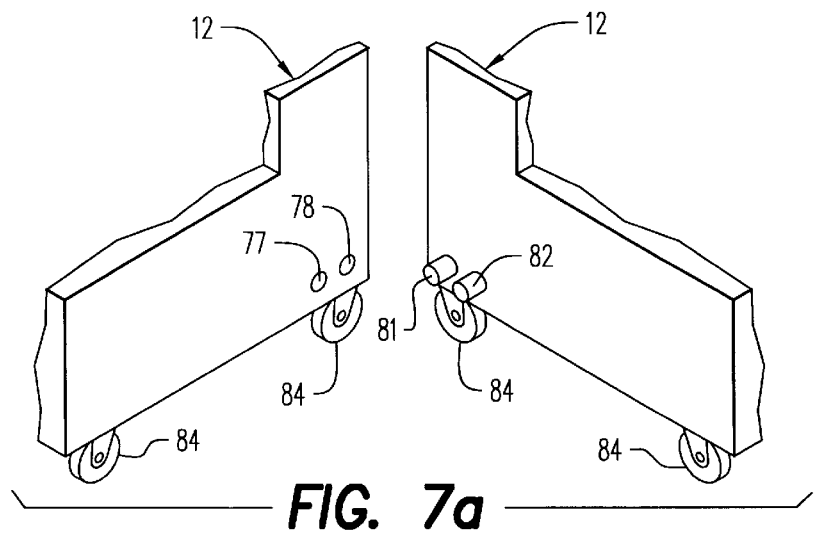

The discharge unit 12f which has an incubation work station 18 and a robotic device 23 is illustrated in FIG. 7. In addition, the unit 12f includes an end wall 71 joined to its canopy 17 by a sealing flange 72. Defined in the end wall 71 is a discharge opening 74 and a door 75 slidable between open and closed positions. The door 75 is opened by a conventional automatic control mechanism 70 after completion of an incubation operation in the work station 18 to allow the robotic device 23 to pass an assay plate 32 through the discharge opening 74 to the uniform position 62 on the reader unit 12g (FIG. 2). As also shown in FIG. 7a, each of the units 12b–12h has on one side wall a pair of female electrical connectors 77, 78 for transmission of, respectively, electrical power and communication signals. The opposite side wall of each unit retains compatible male electrical connectors 81, 82 that are received by the female connectors 77, 78 of an adjacent unit. The connectors 77, 78 and 81, 82 are disposed in uniform locations of each unit 12a–12h so as to accommodate interchangeability thereof and portability is enhanced by supporting rollers 84. In addition, the base of each unit 12b–12f retains a computer 80 and an environmentally controlling electrical heater unit 86 which communicates with the elongated environmental chamber 19 via air input and output openings 87, 88.

Figure 8:
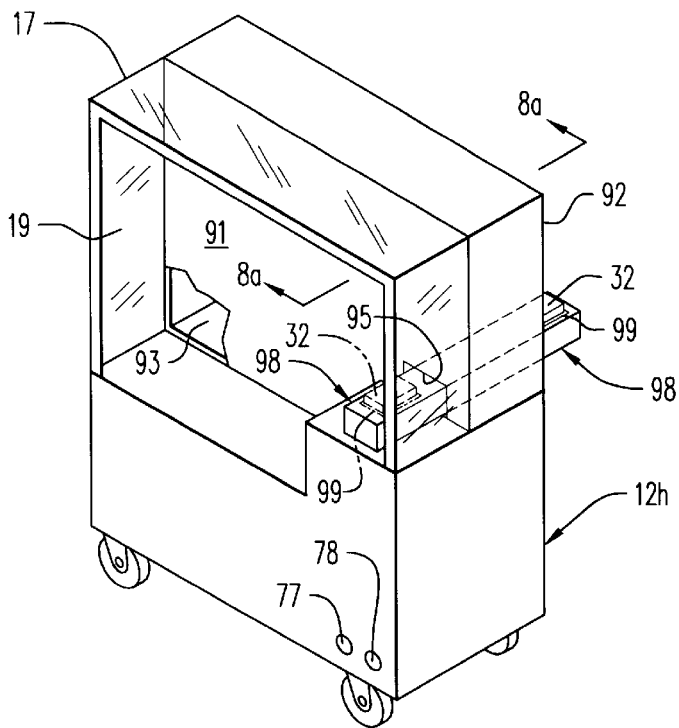
FIG. 8 is a schematic view of an isolation unit which can be used in the system shown in FIGS. 1 and 2.
Figure 8A:
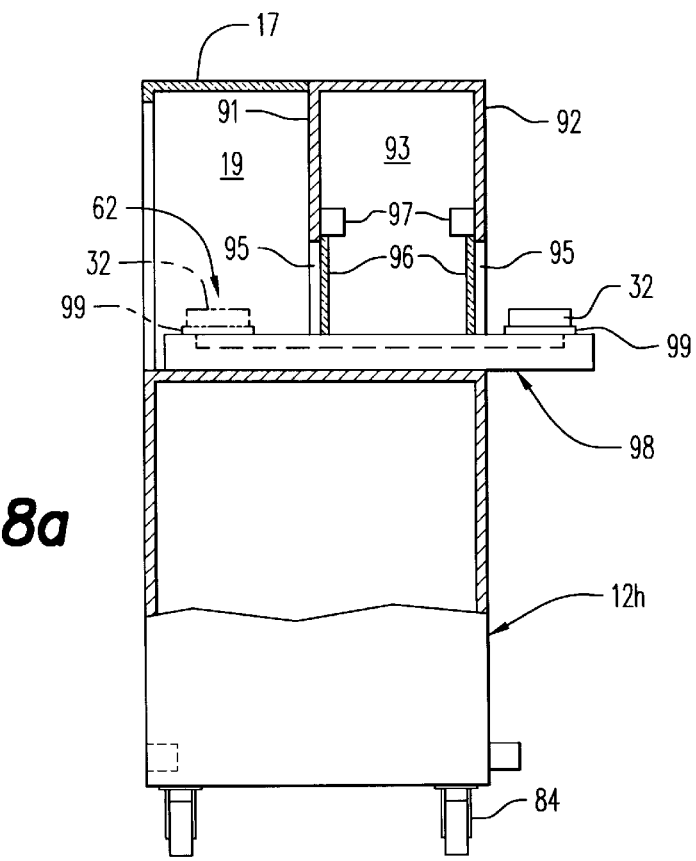
FIG. 8a is a cross-sectional view of the isolation unit shown in FIG. 8.

Illustrated in FIGS. 8 and 8a is an isolation unit 12h which can be selectively inserted into the system 11 when desired for certain screening processes. The isolation unit 12h includes opposite side walls 91, 92 that divide the space under its canopy 17 into an open volume and a closed compartment 93 isolated from the elongated environmental chamber 19. Each of the side walls 91, 92 defines a pass through opening 95 that accommodates transport of assay plates 32 between preceding and succeeding units. The openings 95 are automatically opened and closed by sliding doors 96 operated by conventional automatic door actuators 97. Movement of assay plates 32 through the isolation unit 12h is provided by a transport mechanism 98 (FIG. 8a) which produces reciprocating movement of a rotatable tray 99 between an input receiving position 62 (shown in dashed lines) to a receiving position (shown in solid lines) in a succeeding unit (not shown). After selective insertion into the system 11, the isolation unit 12h can segregate sections of the elongated environmentally controlled chamber 19 which require different environmental conditions.

OPERATION

Prior to use of the system 11, the carousel rack 31 of the assay source section 26 is filled with assay plates 32, the carousel rack 36 of the pipette source section 27 is filled with pipette tip retaining holders 37 and the carousel rack 41 of the test compound source section 28 is filled with compound plates 42. The timer 34 then is set manually to produce operation of the robotic device 33 that sequentially moves assay plates 32 from the rack 31 to the receiving position 62 of the pipette source section 27 at a predetermined rate of, for example, one per minute. In addition, each of the robotic devices 23 is programmed to receive at the same predetermined rate a single assay plate 32 from a preceding unit 12 and to transport a single assay plate 32 to a succeeding unit 12. The selected transport rate of the individual assay plates therefore determines the throughput of the system 11. In the source unit 25, the robotic device 38 alternately and sequentially moves into pockets 48 on the turn-table 47 assay plates from its receiving position 62 and pipette tip holders 37 from the carousel rack 36. The robotic device 38 also sequentially returns used pipette tip holders 37 from the turn-table 47 to vacant positions in the carousel rack 36. In addition, the robotic device 43 alternately and sequentially transports compound plates 42 from the carousel rack 41 to selective pockets 48 on the turn table 47 and transports therefrom completed assay plates 32 through the open door 24 of the entry unit 12b into the receiving position 62 thereof.

Upon registration of a tip holder 37 with the liquid withdrawal and dispensing mechanism 49 (FIG. 4), the array of pipette tips 52 is withdrawn therefrom. Counterclockwise rotation of the turn-table 47 then produces registration of a compound plate 42 and the mechanism utilizes the pipette tips 52 to withdraw the content of the wells 53. The next step-wise and counter-clockwise rotation of the turn-table 47 produces registration of an assay plate 32 and the dispensing mechanism 49 dispenses the content of the pipette tips 52 into the wells 51. A subsequent counterclockwise step rotation of the turn-table 47 moves the completed assay plate 32 from a registration position into a position accessible to the robotic device 43 which transports the completed assay plate 32 to the entry station 12b. Simultaneously therewith, the mechanism 49 loads the used pipette tips 52 into an empty registered holder 37. Such operation of the source unit 20 continues to produce entry into the entry unit 12b of an assay plate 32 at timed intervals established by the timer 34.

During movement of assay plates 32 through the system 11, (FIG. 2) each robot 23 moves assay plates from preceding to succeeding units 12 at the selected rate. The only communication required between adjacent units 12 are signals indicating that an assay plate 32 is available for transport to a succeeding unit or that a position 62 is available to receive an assay plate 32 from a preceding unit. To accommodate the selected assay plate transfer rate, each of the individual units 12b–12f is provided with a work station capacity dependent upon the time period required for completion of its process operation. Thus, the incubation rack of an incubation unit 12d requiring a relatively lengthly incubation period typically will simultaneously accommodate a number of assay plates greater than the number of assay plates simultaneously accommodated by the work stations 18 of either a washing unit 12c or a reagent dispensing unit 12e which require shorter time periods for completion of their process operations. The desired assay plate capacity can be provided in an individual unit by combining available standard processing units of smaller capacity. Because each unit 12b–f is provided with an individual robotic device 23 responsible only for assay plate movement associated with a single process work station, the system 11 can provide a throughput much greater than possible with prior robotic processing systems.

Figure 9:
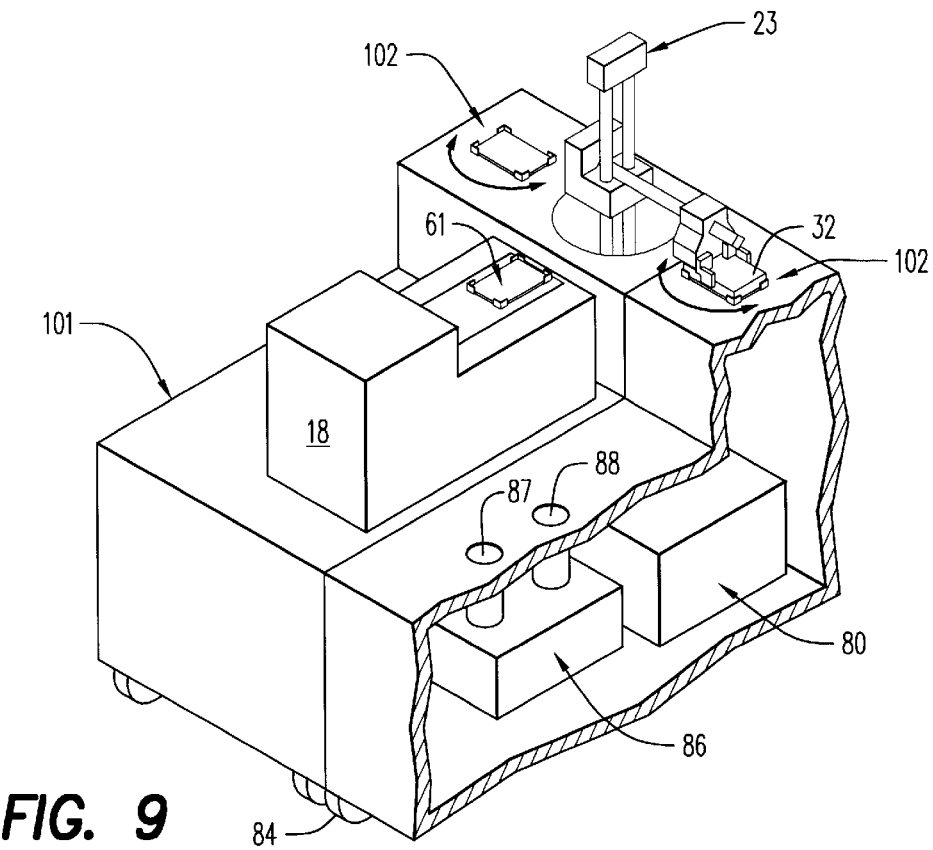
FIG. 9 is a perspective view of another system unit embodiment of the invention.

Illustrated in FIG. 9 is another embodiment unit 101 for use in the system 11. The unit 101 is identical to the units 23 except that it is provided with a discharge position 102 accessible to the robotic device 23 of a succeeding unit rather than the receiving position 62 of the units 12. As in system 11, however, the position 102 is established by a turn-table disposed in a geometrically located portion of each unit 101 so as to enhance therein interchangeability in a complete system.

Figure 10:
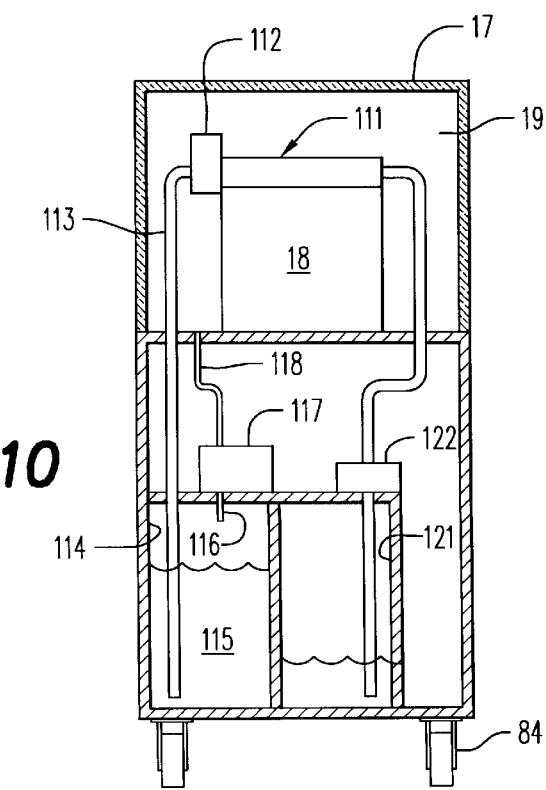
FIG. 10 is a schematic view of a washing unit embodiment of the system shown in FIGS. 1 and 2.

FIG. 10 schematically depicts some of the operational components of a washing unit 12c of the system 11. Mounted under the canopy 17 above the station 18 is a conventional washing head 111 which includes a fluid pump 112. The washing head 111 functions to wash out of the wells 51 of an assay plate 32 (not shown) an unwanted portion of their content. Removed material and wash water 115 together with incidental air from the chamber 19 are circulated by the pump 112 via a tube 113 into a catch reservoir 114 disposed in the lower portion of the unit 12c. Wash water is circulated to the head 111 from a tank 121 by a pump 122. The environmentally conditioned air removed by the pump 112 is withdrawn from the reservoir 114 via a tube 116 by a vacuum pump 117 and returned to the chamber through a tube 118. Accordingly, loss in the washing unit 12c of environmentally conditioned air is prevented.

Obviously, many modifications and variations of the present invention are possible in light of the above teachings. It is to be understood, therefore, that the invention can be practiced otherwise than as specifically described.

What is claimed is:

1. A method for processing products and comprising the steps of:
    providing a processing system comprising a plurality of units each having a work station for simultaneously effecting a specific operation on a plurality of the products;
    equipping each said unit with an associated robotic device;
    interconnecting said units in a predetermined serial arrangement including an initial unit, a plurality of intermediate units and a discharge unit;
    causing said robotic device associated with said initial unit to transport a product from its associated work station to a position accessible to a said robotic device associated with a subsequent said intermediate unit;
    causing said robotic device associated with each said intermediate unit to receive said products from a preceding said unit, to transport said products to said work station associated with its said unit and to transport said products from said associated work station to a position accessible to said robotic device of a subsequent unit;
    causing said robotic device associated with said discharge unit to receive said products from a preceding said intermediate unit, to transport said products to said work station associated with its said discharge unit and to transport said products to a discharge area; and
    effecting on the products in each said work station said operation associated therewith.

2. A method for processing products according to claim 1 wherein said interconnecting step comprises interconnecting at least a given number of said units in a rectilinear array.

3. A method of processing products according to claim 1 wherein said interconnecting step comprises the steps of interconnecting some of said units into a first rectilinear array and interconnecting other said units in a second array disposed transverse to said first array.

4. A method of processing products according to claim 1 wherein said units are interchangeable units.

5. A method according to claim 1 wherein each said unit is supported on rollers to provide mobility.

6. A method for processing products according to claim 1 wherein the system is a chemical screening system and the products are chemical assays.

7. A method for processing products according to claim 6 including the steps of loading said chemical assays into individual receptacles prior to said causing steps, and wherein said operations comprise incubation, receptacle washing and reagent addition operations.

8. A method for processing products according to claim 1 including the step of changing in at least one of said intermediate units the orientation of said products received in said position.

9. A robotic chemical screening system for processing chemical assays and comprising:
    a plurality of units arranged to sequentially receive the assays and each comprising work station for effecting a specific operation on the assays, and
    a robotic device associated with each said unit and operable to sequentially obtain each said assay from a preceding said unit, to transport each said assay to said work station of its associated unit and to transport each said assay from said associated work station to a position accessible to a said robotic device of a succeeding said unit.

10. A robotic system according to claim 9 wherein said units are modular, interchangeable units.

11. A robotic system according to claim 10 wherein said position is disposed in a uniform geometrically located portion of each unit.

12. A robotic system according to claim 11 wherein said position is disposed on said associated unit.

13. A robotic system according to claim 11 wherein said position is disposed on said succeeding unit.

14. A robotic system according to claim 11 wherein at least a given number of said units are interconnected in a rectilinear array that accommodates movement of the products in a rectilinear path.

15. A robotic system according to claim 14 wherein each said unit comprises electrical connector means automatically coupled to said connector means of adjacent units in response to interconnection thereof.

16. A robotic system according to claim 15 wherein said connector means of each unit comprise a pair of connectors shaped and arranged for connection with, respectively, said connectors of adjacent said units.

17. A robotic processing system for processing a plurality of products, said system comprising:

a plurality of modular, interchangeable units arranged to sequentially receive the products and each comprising a work station for simultaneously effecting a specific operation on a plurality of the products; at least a given number of said units being interconnected in a rectilinear array that accommodates movement of the products in a rectilinear path and, each unit having a pair of connectors shaped and arranged for connection with, respectively, said connectors of adjacent said units; and a robotic device associated with each said unit and operable to sequentially obtain each said product from a preceding said unit, to transport each said product to said work station of its associated unit and to transport each said product from said associated work station to a position accessible to a said robotic device of a succeeding said unit, said position being disposed in a uniform geometrically located portion of each unit.

18. A robotic system according to claim 17 wherein said connectors are disposed in uniform locations of each unit.

19. A robotic system according to claim 18 wherein each said unit is supported on rollers to provide mobility.

20. A robotic system according to claim 19 wherein said units include a corner unit connected to one end of said rectilinear array and shaped and arranged to provide movement of the products in a direction transverse to said rectilinear path.

21. A robotic processing system for processing a plurality of products, said system comprising:

a plurality of units arranged to sequentially receive the products and each comprising a work station for simultaneously effecting a specific operation on a plurality of the products, each unit having a pair of connectors shaped and arranged for connection with, respectively, said connectors of adjacent said units; and a robotic device associated with each said unit and operable to sequentially obtain each said product from a preceding said unit, to transport each said product to said work station of its associated unit and to transport each said product from said associated work station to a position accessible to a said robotic device of a succeeding said unit.

22. A robotic system according to claim 21 wherein said connectors are disposed in uniform locations of each unit.

23. A robotic processing system for processing a plurality of products, said system comprising:

a plurality of units arranged to sequentially receive the products and each comprising a work station for simultaneously effecting a specific operation on a plurality of the products, at least a given number of said units are interconnected in a rectilinear array that accommodates movement of the products in a rectilinear path, and said units include a corner unit connected to one end of said rectilinear array and shaped and arranged to provide movement of the products in a direction transverse to said rectilinear path; and a robotic device associated with each said unit and operable to sequentially obtain each said product from a preceding said unit, to transport each said product to said work station of its associated unit and to transport each said product from said associated work station to a position accessible to a said robotic device of a succeeding said unit.

* * * * *